United States Patent
Kim et al.

(10) Patent No.: US 9,110,156 B2
(45) Date of Patent: Aug. 18, 2015

(54) APPARATUS AND SYSTEM FOR MEASURING VELOCITY OF ULTRASOUND SIGNAL

(75) Inventors: Gyu Won Kim, Gyeonggi-do (KR); Ho Seop Jeong, Gyeonggi-do (KR); Kyoung Joong Min, Seoul (KR)

(73) Assignee: SAMSUNG ELECTRO-MECHANICS CO., LTD., Gyunggi-Do (KR)

( * ) Notice: Subject to any disclaimer, the term of this patent is extended or adjusted under 35 U.S.C. 154(b) by 1060 days.

(21) Appl. No.: 13/181,450

(22) Filed: Jul. 12, 2011

(65) Prior Publication Data

US 2012/0011935 A1    Jan. 19, 2012

(30) Foreign Application Priority Data

Jul. 13, 2010   (KR) .......................... 10-2010-0067388

(51) Int. Cl.
*G01N 29/44*    (2006.01)
*G01S 7/52*     (2006.01)
*A61B 8/00*     (2006.01)

(52) U.S. Cl.
CPC ............. *G01S 7/52049* (2013.01); *A61B 8/585* (2013.01); *G01N 29/44* (2013.01); *G01S 7/52077* (2013.01)

(58) Field of Classification Search
CPC ............ G01N 29/44; A61B 8/00; A61B 8/58; A61B 8/585
USPC ............ 73/602, 597, 598; 600/437, 447, 453, 600/455; 382/128, 130, 131
See application file for complete search history.

(56) References Cited

U.S. PATENT DOCUMENTS

| | | | | |
|---|---|---|---|---|
| 5,415,173 A * | 5/1995 | Miwa et al. | .................... | 600/447 |
| 5,638,820 A * | 6/1997 | Chen et al. | .................... | 600/437 |
| 6,305,225 B1 * | 10/2001 | Bae et al. | ........................ | 73/602 |
| 6,515,657 B1 * | 2/2003 | Zanelli | .......................... | 345/419 |
| 8,002,705 B1 * | 8/2011 | Napolitano et al. | .......... | 600/437 |
| 8,475,381 B2 * | 7/2013 | Kakee et al. | .................. | 600/443 |
| 2001/0017937 A1 * | 8/2001 | Bonnefous | ................... | 382/128 |
| 2003/0097065 A1 * | 5/2003 | Lee et al. | ..................... | 600/437 |
| 2007/0083110 A1 * | 4/2007 | Lin et al. | ...................... | 600/437 |
| 2009/0099451 A1 * | 4/2009 | Nakaya et al. | ................. | 600/443 |
| 2009/0175557 A1 * | 7/2009 | Lankoande et al. | .......... | 382/275 |
| 2011/0190632 A1 * | 8/2011 | Kim et al. | .................... | 600/443 |

FOREIGN PATENT DOCUMENTS

| | | |
|---|---|---|
| JP | 2008-161208 A | 7/2008 |
| JP | 2008-264531 | 11/2008 |
| KR | 10-0875203 B1 | 12/2008 |
| KR | 10-2010-0016731 A | 2/2010 |
| KR | 10-0947827 | 3/2010 |
| KR | 10-0948045 B1 | 3/2010 |

* cited by examiner

*Primary Examiner* — Laura Martin
*Assistant Examiner* — Rose M Miller
(74) *Attorney, Agent, or Firm* — Bracewell & Giuliani LLP; Brad Y. Chin

(57) ABSTRACT

Disclosed herein are an apparatus and a method for measuring velocity of an ultrasound signal. The apparatus for measuring velocity of an ultrasound signal according to an exemplary embodiment of the present invention includes a transmitting module transmitting ultrasound signals to targets; a receiving module receiving the ultrasound signals reflected from the targets; an image generating module using the received ultrasound signals to generate a plurality of ultrasonic images having different sound velocities; and a sound velocity determining module using the plurality of generated ultrasonic images to determine optimal sound velocity for scanning the targets.

6 Claims, 2 Drawing Sheets

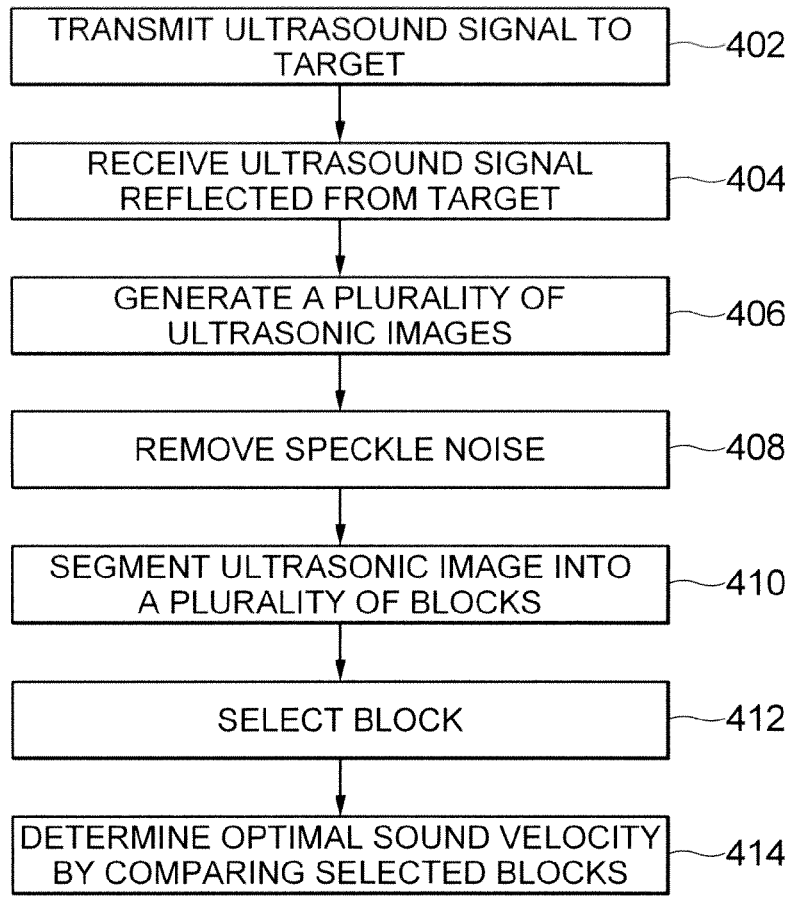

APPARATUS AND SYSTEM FOR MEASURING VELOCITY OF ULTRASOUND SIGNAL

CROSS REFERENCE TO RELATED APPLICATION

This application claims the benefit of Korean Patent Application No. 10-2010-0067388, titled on Jul. 13, 2010, entitled "Apparatus and System for Measuring Velocity of Ultrasound Signal", which is hereby incorporated by reference in its entirety into this application.

BACKGROUND OF THE INVENTION

1. Technical Field

The present invention relates to a technology capable of measuring optimal velocity of an ultrasound signal in an ultrasonic image system.

2. Description of the Related Art

An ultrasonic image system is defined as a system that transmits ultrasound signals to targets and then, receives the ultrasound signals reflected from the targets and converts and outputs them into images. Since the ultrasonic image system is harmless to a human body and can obtain a relatively accurate image, it has been used in various fields.

Recently, research into increasing resolution of the ultrasonic images has been continuously conducted. Generally, the medical ultrasonic image system receives ultrasound signals and outputs them as images under the assumption that the ultrasound signal propagating velocity in the human body is 1540 m/s. However, since the velocity of the ultrasound signal is varied depending on the type of media, there is a problem in that the quality of output image is deteriorated when the velocity of the ultrasound signal is fixed as described above. Therefore, a need exists for research into determining the optimal velocity of the ultrasound signal in real time according to the targets.

SUMMARY OF THE INVENTION

An object of the present invention is to improve the quality of an image from an ultrasonic image apparatus by generating a plurality of ultrasonic images measured at different velocities from targets and measuring optimal sound velocity using the generated ultrasonic images.

According to an exemplary embodiment of the present invention, there is provided an apparatus for measuring velocity of an ultrasound signal, including: a transmitting module transmitting ultrasound signals to targets; a receiving module receiving the ultrasound signals reflected from the targets; an image generating module using the received ultrasound signals to generate a plurality of ultrasonic images having different velocities; and a sound velocity determining module using the plurality of generated ultrasonic images to determine optimal sound velocity for scanning the targets.

The sound velocity determining module may include: a noise removing unit removing speckle noises from the plurality of generated ultrasonic images; an image segmenting unit segmenting the plurality of ultrasonic images from which noise are removed into each of the plurality of blocks; a block selector selecting a predetermined number of blocks from the plurality of segmented blocks; and a sound velocity determining unit comparing the blocks of the plurality of ultrasonic images selected in the block selector to determine the optimal sound velocity for scanning the targets.

The block selector may detect edge regions for each of the plurality of segmented blocks, sum the luminance of the edge regions detected for each block, and select a predetermined number of blocks in an order of the large summed luminance The number of blocks selected in the block selector may be defined according to the following Equation.

$$\text{Block Number} = \frac{\text{Total\_L\_AVG}/N}{K}$$

(Where, Total_L_AVG represents an average luminance of the edge region of the ultrasonic image, N represents the number of entire blocks, and K represents an adjustment factor.)

The sound velocity determining unit may detect the edge regions of blocks selected for each ultrasonic image, sum the luminance of the detected edge regions, and compare the luminance of the edge regions summed for each ultrasonic image to determine the sound velocity of the ultrasonic images having the smallest luminance in the summed edge regions as the optimal sound velocity for scanning the targets.

According to another exemplary embodiment of the present invention, there is provided a method for measuring velocity of an ultrasound signal, including: transmitting ultrasound signals to targets, in an apparatus for measuring velocity of an ultrasound signal; receiving the ultrasound signals reflected from the targets, in the apparatus for measuring velocity of an ultrasound signal; generating a plurality of ultrasonic images having different sound velocities by using the received ultrasound signals, in the apparatus for measuring velocity of an ultrasound signal; and determining optimal sound velocity for scanning the targets by using plurality of generated ultrasonic images, in the apparatus for measuring velocity of an ultrasound signal.

The determining the sound velocity may include: removing speckle noise from the plurality of generated ultrasonic images; segmenting each of the plurality of ultrasonic images from which noise are removed into a plurality of blocks; selecting a predetermined number of blocks from the plurality of segmented blocks; and comparing the blocks of the plurality of ultrasonic images selected in the block selector to determine the optimal sound velocity for scanning the targets.

The selecting the block may detect edge regions for each of the plurality of segmented blocks, sum the luminance of the edge regions detected for each block, and select predetermined number of blocks in an order of the large summed luminance.

The number of blocks selected at the selecting of the block may be defined according to the following Equation.

$$\text{Block Number} = \frac{\text{Total\_L\_AVG}/N}{K}$$

(Where, Total_L_AVG represents an average luminance of the edge region of the ultrasonic image, N represents the number of entire blocks, and K represents an adjustment factor.)

The determining the sound velocity may detect the edge regions of blocks selected for each ultrasonic image, sum the luminance of the detected edge regions, and compare the luminance of the edge regions summed for each ultrasonic image to determine the sound velocity of the ultrasonic images having the smallest luminance in the summed edge region as the optimal sound velocity for scanning the targets.

BRIEF DESCRIPTION OF THE DRAWINGS

FIG. 3 is a diagram for explaining ultrasonic image segmentation of an image segmenting unit 202 according to an exemplary embodiment of the present invention; and FIG. 4 is a flow chart showing a method 400 for measuring velocity of an ultrasound signal according to an exemplary embodiment of the present invention.

DESCRIPTION OF THE PREFERRED EMBODIMENTS

Hereinafter, exemplary embodiments of the present invention be described with reference to the accompanying drawings. However, the exemplary embodiments are described by way of examples only and the present invention is not limited thereto.

In the following description, when it is determined that the detailed description of the conventional technology related to the present invention would confuse the gist of the present invention, such a description may be omitted. Terms used in the specification and claims herein are defined by considering the functions thereof in the present invention so that they may be varied according to a user's and an operator's intentions or practices. Therefore, the definitions thereof should be construed based on the contents throughout the specification.

As a result, the spirit of the present invention is determined by the claims and the following exemplary embodiments may be provided to efficiently describe the spirit of the present invention to those skilled in the art.

Figure 1:
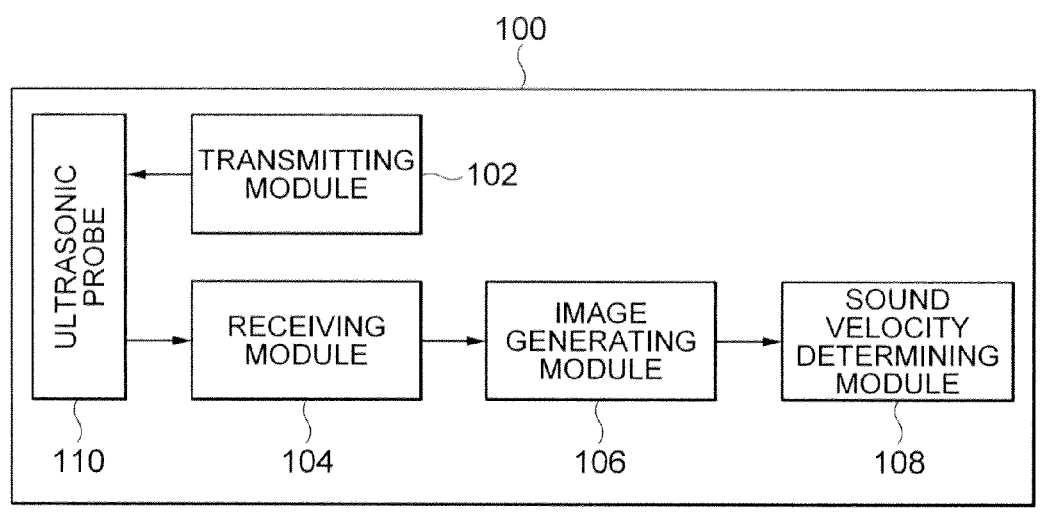
FIG. 1 is a block diagram of an apparatus 100 for measuring velocity of an ultrasound signal according to an exemplary embodiment of the present invention.

FIG. 1 is a block diagram of an apparatus 100 for measuring velocity of an ultrasound signal according to an exemplary embodiment of the present invention.

As shown, the apparatus 100 for measuring velocity of an ultrasound signal according to an exemplary embodiment of the present invention include a transmitting module 102, a receiving module 104, an image generating module 106, and a sound velocity determining module 108.

The transmitting module 102 transmits ultrasound signals to targets by using an ultrasonic probe 110. In this configuration, the transmitting module 102 may transmit the ultrasound signals at a predetermined fixing sound velocity (for example, 1540 m/s). In this case, the fixing sound velocity may be set according to characteristics of media configuring targets.

Alternatively, the transmitting module 102 may vary sound velocity within a predetermined sound velocity range (for example, 1400 m/s to 1590 m/s) to transmit a plurality of ultrasound signals. For example, the transmitting module 102 may be configured to transmit the ultrasound signals by varying the sound velocity at a unit of 10 m/s, such as 1400 m/s, 1410 m/s, 1420 m/s, or the like, within the above-mentioned range.

The receiving module 104 receives the ultrasound signals that are reflected from the targets and transferred to the ultrasonic probe 110.

The image generating module 106 generates the plurality of ultrasonic images having different sound velocities by using the ultrasound signals received through the receiving module 104. When the transmitting module 102 transmits the ultrasound signals at the predetermined fixing sound velocity, the image generating module 106 may process the reflected ultrasound signals to generate a plurality of images having different sound velocities within the predetermined sound velocity range (for example, 1400 m/s to 1590 m/s). For example, the images having sound velocities such as 1400 m/s, 1410 m/s, 1420 m/s, or the like by using the ultrasound signals received at 1540 m/s. In addition, when the transmitting module 102 transmits the plurality of ultrasound signals having different sound velocities, the image generating module 106 may generate the plurality of transmitted images corresponding to each sound velocity without being subjected to a separate process. The processing of ultrasound signals and the generation of images are known to those skilled and therefore, the detailed description thereof will be omitted.

The sound velocity determining module 108 determines the optimal sound velocity for scanning the targets by using the plurality of ultrasonic images generated from the image generating module 106. The optimal sound velocity for scanning the targets implies the sound velocity capable of most visually definitively identifying the targets. That is, similar to focusing to the subject by controlling a lens of a camera, the definitive images like being "focused" to the targets can be obtained by controlling the velocity of the ultrasound signal even in the ultrasonic image apparatus. In this configuration, it is the sound velocity determining module 108 that determines the sound velocity.

When the optimal sound velocity of the target is determined in the sound velocity determining module 108, the sound velocity determining module 108 may transmit the determined optimal sound velocity information to the transmitting module 102. In this case, the transmitting module 102 may transmit the ultrasound signals set as the optimal sound velocity to the targets to generate the images of the targets. Alternatively, the sound velocity determining module 108 may transmit the determined optimal sound velocity information to the image generating module 106. In this case, the image generating module 106 processes the received ultrasound signals at the fixed sound velocity so as to be met with the optimal sound velocity, thereby making it possible to generate the images of the targets.

Figure 2:
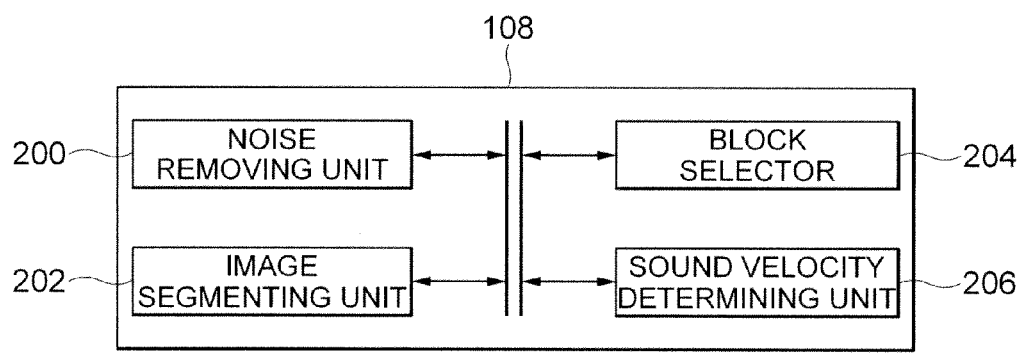
FIG. 2 is a diagram showing a detailed configuration of a sound velocity determining module 108 according to an exemplary embodiment of the present invention.

FIG. 2 is a diagram showing a detailed configuration of the sound velocity determining module 108 according to an exemplary embodiment of the present invention.

As shown, the sound velocity determining module 108 according to an exemplary embodiment of the present invention includes a noise removing unit 200, an image segmenting unit 202, a block selector 204, and a sound velocity determining unit 206.

The noise removing unit 200 removes speckle noise from the plurality of ultrasonic images generated in the image generating module 106. Generally, when noise is not removed from the ultrasonic images, it is very difficult to analyze images due to the speckle, etc. Therefore, noise should be first removed in order to analyze images.

The image segmenting unit 202 segments the plurality of ultrasonic images from which noise is removed into N×N domains as shown in FIG. 3, thereby generating a plurality of blocks. FIG. 3 shows an example of segmenting the ultrasonic images into 5×5 but the number of segmented blocks may be increased or reduced, if necessary. Further, as shown, the blocks segmented may be numbered to differentiate each block.

The reason for segmenting the ultrasonic images is to reduce the calculating amount for analyzing the ultrasonic images. When analyzing the entire image generated in the image generating module 106, a lot of calculation is needed and the corresponding hardware needs also to be supported. Therefore, the exemplary embodiment of the present invention segments the ultrasonic images and selects and analyzes only the necessary blocks of the segmented blocks, thereby making it possible to efficiently reduce the calculation amount.

The block selector 204 selects a predetermined number of blocks to be used to determine the sound velocity among the plurality of blocks segmented in the image segmenting unit 202. In order to select the blocks, the block selector 204 detects the edge regions of each block that is first segmented. The edge region is a portion corresponding to the edge of the target on the screen, which is shown on the screen brighter than a portion out of the edge region. As described above, when the edge region of each block is detected, the block selector 204 sums the luminance of the edge regions detected for each block and selects a predetermined number of blocks in an order of the large summed value first. The reason for selecting the blocks in which the value obtained by summing the luminance of the edge region is large is that the blocks having the large summed value occupies a considerable portion of the edge region in all the blocks. That is, in the present invention, since the measurement of the sound velocity is made by comparing the edge regions of each ultrasonic image, it is important to select the blocks having a large number of edge regions in order to accurately measure the sound velocity.

Meanwhile, the number of blocks selected in the block selector 204 depends on the following Equation.

$$\text{Block Number} = \frac{\text{Total\_L\_AVG}/N}{K}$$

In this case, Total_L_AVG may represent the average luminance of the edge region of the ultrasonic image, N may represent the number of entire blocks, and K may represent an adjustment factor, which may be appropriately defined according to the type of targets.

Next, the sound velocity determining unit 206 compares the blocks selected in the block selector 204 for each of the plurality of ultrasonic images to determine the optimal sound velocity for scanning the targets.

The optimal sound velocity determination in the sound velocity determining unit 206 is made as follows. First, the edge regions of the blocks selected in the block selector 204 are detected for each ultrasonic image. In this case, in order to detect the edge region, the same algorithm calculated for detecting the edge region in the block selector 204 may also be used. When the edge region is detected, the luminance of the edge regions of the blocks selected for each ultrasonic image is summed. In other words, the entire luminance of the edge regions is summed for each ultrasonic image rather than for each block unit at the current process. As described above, the luminance of the edge regions is summed for each ultrasonic image, the values summed for each ultrasonic image are compared to determine sound velocity used to generate the ultrasonic image having the smallest summed value as the optimal sound velocity for scanning the target. As such, the reason for selecting the image having the smallest summed value of the edge region is that the edge region is thinly shown as the target is definitively shown in the image. On the other hand, when the target is shown dimly, the edge region is shown dimly and thickly. Therefore, when the blocks are present at the same position, the target that is definitively shown as the sum of the luminance of the edge regions is small.

FIG. 4 is a flow chart showing a method 400 for measuring velocity of an ultrasound signal according to an exemplary embodiment of the present invention.

First, the apparatus 100 for measuring velocity of an ultrasound signal transmits the ultrasound signals to the target (402).

Next, the apparatus 100 for measuring velocity of an ultrasound signal receives the ultrasound signals reflected from the target (404) and uses the received ultrasound signals to generate the plurality of ultrasonic images having different sound velocities (406).

Next, the apparatus 100 for measuring velocity of an ultrasound signal removes the speckle noise from the plurality of ultrasonic images (408) and segments the plurality of ultrasonic images from which noise is removed into each of the plurality of blocks (410).

Next, the apparatus 100 for measuring velocity of an ultrasound signal selects the predetermined blocks from the plurality of segmented blocks (412) according to the above-mentioned method and compares the blocks of the plurality of ultrasonic images selected in the block selector to determine the optimal sound velocity for scanning the target (414).

According to the exemplary embodiments of the present invention, the optimal velocity of an ultrasound signal can be determined according to the targets, thereby making it possible to obtain the optimal ultrasonic images regardless of the characteristics of the targets. To this end, the present invention segments the ultrasonic images into the plurality of blocks and performs the analysis only in the necessary blocks, thereby making it possible to remarkably reduce the calculation amount for measuring the velocity of the ultrasound signal.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

Accordingly, the scope of the present invention is not construed as being limited to the described embodiments but is defined by the appended claims as well as equivalents thereto.

What is claimed is:

1. An apparatus for measuring velocity of an ultrasound signal, comprising:
    a transmitting module transmitting ultrasound signals to targets;
    a receiving module receiving the ultrasound signals reflected from the targets;
    an image generating module using the received ultrasound signals to generate a plurality of ultrasonic images having different sound velocities; and
    a sound velocity determining module using the plurality of generated ultrasonic images to determine optimal sound velocity for scanning the targets,
    wherein the sound velocity determining module comprises:
        a noise removing unit removing speckle noises from the plurality of generated ultrasonic images,
        an image segmenting unit segmenting the plurality of ultrasonic images from which noise is removed into each of the plurality of blocks, a block selector selecting a predetermined number of blocks from the plurality of segmented blocks, and a sound velocity determining unit comparing the blocks of the plurality of ultrasonic images selected in the block selector to determine the optimal sound velocity for scanning the targets, wherein the sound velocity determining unit detects the edge regions of blocks selected for each ultrasonic image, sums the luminance of the detected edge regions, and compares the luminance of the edge regions summed for each ultrasonic image to determine the sound velocity of the ultrasonic images having the smallest luminance in the summed edge regions as the optimal sound velocity for scanning the targets.

2. The apparatus for measuring velocity of an ultrasound signal according to claim 1, wherein the block selector detects edge regions for each of the plurality of segmented blocks, sums the luminance of the edge regions detected for each block, and selects a predetermined number of blocks in an order of the large summed luminance.

3. The apparatus for measuring velocity of an ultrasound signal according to claim 2, wherein the number of blocks selected in the block selector is defined according to the following Equation $$\text{Block Number} = \frac{\text{Total\_L\_AVG}/N}{K}$$

(Where, Total_L_AVG represents an average luminance of the edge region of the ultrasonic image, N represents the number of entire blocks, and K represents an adjustment factor.)

4. A method for measuring velocity of an ultrasound signal, comprising:

transmitting ultrasound signals to targets, in an apparatus for measuring velocity of an ultrasound signal;

receiving the ultrasound signals reflected from the targets, in the apparatus for measuring velocity of an ultrasound signal;

generating a plurality of ultrasonic images having different sound velocities by using the received ultrasound signals, in the apparatus for measuring velocity of an ultrasound signal; and determining optimal sound velocity for scanning the targets by using the plurality of generated ultrasonic images, in the apparatus for measuring velocity of an ultrasound signal, wherein the determining the sound velocity comprises:

removing speckle noise from the plurality of generated ultrasonic images;

segmenting each of the plurality of ultrasonic images from which noise is removed into a plurality of blocks;

selecting a predetermined number of blocks from the plurality of segmented blocks; and comparing the blocks of the plurality of ultrasonic images selected in the block selector to determine the optimal sound velocity for scanning the targets, wherein the determining the sound velocity detects the edge regions of blocks selected for each ultrasonic image, sums the luminance of the detected edge regions, and compares the luminance of the edge regions summed for each ultrasonic image to determine the sound velocity of the ultrasonic images having the smallest luminance in the summed edge region as the optimal sound velocity for scanning the targets.

5. The method for measuring velocity of an ultrasound signal according to claim 4, wherein the selecting the block detects edge regions for each of the plurality of segmented blocks, sums the luminance of the edge regions detected for each block, and selects a predetermined number of blocks in an order of the large summed luminance.

6. The method for measuring velocity of an ultrasound signal according to claim 5, wherein the number of blocks selected at the selecting the block is defined according to the following Equation $$\text{Block Number} = \frac{\text{Total\_L\_AVG}/N}{K}$$

(Where, Total_L_AVG represents an average luminance of the edge region of the ultrasonic image, N represents the number of entire blocks, and K represents an adjustment factor.)

* * * * *